(12) United States Patent
Srinivasan et al.

(10) Patent No.: US 7,887,484 B2
(45) Date of Patent: Feb. 15, 2011

(54) AUTOMATIC VELOCITY SCALE IDENTIFICATION FOR MEDICAL DIAGNOSTIC ULTRASOUND

(75) Inventors: Seshadri Srinivasan, Mountain View, CA (US); Bhaskar Ramamurthy, Los Altos, CA (US); Ismayil M. Guracar, Redwood City, CA (US); Patrick J. Phillips, Sunnyvale, CA (US); Rickard C. Loftman, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1587 days.

(21) Appl. No.: 11/202,676

(22) Filed: Aug. 12, 2005

(65) Prior Publication Data
US 2007/0038083 A1 Feb. 15, 2007

(51) Int. Cl.
*A61B 8/00* (2006.01)
(52) U.S. Cl. ........................... 600/437; 600/443
(58) Field of Classification Search ......... 600/437–449, 600/455; 73/602, 625–626
See application file for complete search history.

(56) References Cited

U.S. PATENT DOCUMENTS

| | | | |
|---|---|---|---|
| 4,799,490 A * | 1/1989 | Namekawa | 600/455 |
| 4,844,082 A * | 7/1989 | Fukukita et al. | 600/442 |
| 5,363,851 A | 11/1994 | Hall et al. | |
| 5,443,071 A | 8/1995 | Banjanin et al. | |
| 5,555,534 A | 9/1996 | Maslak et al. | |
| 5,581,517 A | 12/1996 | Gee et al. | |
| 5,623,928 A | 4/1997 | Wright et al. | |
| 5,675,554 A | 10/1997 | Cole et al. | |
| 5,685,308 A | 11/1997 | Wright et al. | |
| 5,800,358 A | 9/1998 | Webb et al. | |
| 5,891,040 A | 4/1999 | Grenon et al. | |
| 5,895,358 A | 4/1999 | Becker et al. | |
| 5,921,932 A | 7/1999 | Wright et al. | |
| 6,017,309 A | 1/2000 | Washburn et al. | |
| 6,045,507 A | 4/2000 | Muzilla et al. | |
| 6,071,241 A | 6/2000 | Washburn et al. | |
| 6,110,119 A | 8/2000 | Hall | |
| 6,120,451 A | 9/2000 | Washburn et al. | |
| 6,123,672 A | 9/2000 | Miller et al. | |
| 6,126,605 A | 10/2000 | Washburn et al. | |
| 6,162,176 A | 12/2000 | Washburn et al. | |
| 6,176,828 B1 | 1/2001 | Becker et al. | |
| 6,221,019 B1 * | 4/2001 | Kantorovich | 600/449 |
| 6,315,728 B1 | 11/2001 | Muzilla et al. | |
| 6,379,306 B1 | 4/2002 | Washburn et al. | |
| 6,478,742 B1 | 11/2002 | Kataoka | |
| 6,500,125 B1 | 12/2002 | Muzilla et al. | |

(Continued)

*Primary Examiner*—Eric F Winakur
*Assistant Examiner*—Lawrence N Laryea (57) ABSTRACT

Velocity scale is automatically determined for ultrasound imaging. Receive signals corresponding to different pulse repetition intervals are used to estimate velocities. The different velocities are used to determine the velocity scale. For example, the different pulse repetition intervals are obtained by selecting different sets of signals from a group of signals for a scan line. As another example, the different pulse repetition intervals are obtained by transmitting for a scan line with changing, such as increasing, pulse repetition intervals. The lower pulse repetition interval of a pair of intervals associated with a sign change in the phase is used for the velocity scale. In yet another example, at least two demodulation frequencies are used for a broadband transmit in at least two sets, each set with a different pulse repetition interval. Velocities are estimated for a greater number of pulse repetition intervals than transmitted using the broadband pulses.

29 Claims, 3 Drawing Sheets

U.S. PATENT DOCUMENTS 6,733,454 B1 * 5/2004 Bakircioglu et al. ........ 600/453
2004/0254467 A1 * 12/2004 Jackson ...................... 600/450
2005/0033175 A1 2/2005 Lee et al.
2005/0131300 A1 * 6/2005 Bakircioglu et al. ........ 600/453

* cited by examiner

$S(m,n) = MAX[I^i(m,n)]$ FOR $1 \leq i \leq 4$

AUTOMATIC VELOCITY SCALE IDENTIFICATION FOR MEDICAL DIAGNOSTIC ULTRASOUND

BACKGROUND

This present embodiments relate to identifying velocity scale. In medical diagnostic ultrasound imaging, the velocity scale is set to prevent aliasing.

Medical diagnostic ultrasound imaging systems perform autocorrelation between sets of received data to determine an average phase shift for flow or tissue velocity imaging. In Doppler processing, the phase shift represents the velocity of tissue or fluid. The velocity scale is selected to prevent aliasing. The velocity scale may be assigned as a preset for a given type of imaging or application. For example, different velocity scale presets may be provided for cardiac imaging than for imaging a thyroid.

The presets may be incorrect given the patient being imaged or other system settings. The user may adjust the velocity scale or other user input for changing the velocity scale. Based on expected image characteristics, the user adjust the scale to be sufficiently large to avoid aliasing but sufficiently small to maximize the dynamic range of velocities. However, user adjustment may be time consuming, difficult or undesired, resulting in longer scan times or sub-optimal image quality. When the imaging is changed, such as switching to imaging a different region of the patient, the previously selected velocity scale may be sub-optimal. The user may need to again manually adjust the velocity scale.

Automated anti-aliasing may be provided. U.S. Published Application No. 20040254467, the disclosure of which is incorporated by reference, discloses identification of the pulse repetition frequency by unwrapping phase information. Different possible velocities are determined from velocity estimates by applying different baseline shifts. The possible velocities with a minimal variance are selected as the unaliased velocities.

BRIEF SUMMARY

By way of introduction the preferred embodiments described below include a methods, systems and instructions for determining velocity scale for ultrasound imaging. Receive signals corresponding to different pulse repetition intervals are used to estimate velocities. The different velocities are used to determine the velocity scale. In one embodiment, the different pulse repetition intervals are obtained by selecting different sets of signals from a group of signals for a scan line. In another embodiment, the different pulse repetition intervals are obtained by transmitting for a scan line with changing, such as increasing, pulse repetition intervals. The lower pulse repetition interval of a pair of intervals associated with a sign change in the phase is used for the velocity scale. In yet another embodiment, at least two demodulation frequencies are obtained from broadband transmit pulses in at least two sets, each set with a different pulse repetition interval. Velocities are estimated for a greater number of pulse repetition intervals than transmitted using the broadband pulses.

In a first aspect, a method is provided for determining velocity scale for ultrasound imaging. Signals responsive to multiple transmissions along a substantially same scan line are obtained. First and second velocities are estimated from the signals as a function of first and second different pulse repetition intervals, respectively. A velocity scale is determined as a function of the first and second velocities.

In a second aspect, a system is provided for determining velocity scale for ultrasound imaging. A memory is operable to store signals responsive to multiple transmissions along a substantially same scan line. A velocity estimator is operable to estimate first and second velocities from the signals as a function of first and second different pulse repetition intervals, respectively. A processor is operable to determine a velocity scale as a function of the first and second velocities.

In a third aspect, a method is provided for determining velocity scale for ultrasound imaging. Signals responsive to at least two demodulation frequencies along a substantially same scan line are obtained. A velocity scale is determined as a function of the signals.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The velocity scale setting (pulse repetition interval) is automatically identified for color flow or tissue imaging. A sparsely sampled pilot flow sample group with a long flow sample count is fired, and flow parameters are estimated for several pulse repetition interval (PRI) values within the flow sample group. Velocity and the energy values obtained from the collection of velocity and energy estimates are used to identify the scale setting and/or regions of valid flow or motion within the color region-of-interest (ROI). By automatically determining the velocity scale, user adjustment of the scale setting may be limited or eliminated. The scanning time for an examination may be reduced. If the imaging region or settings change, the velocity scale may be reset with minimal user adjustment. Automatic velocity identification and display may be used to minimize aliasing in carotid flow, improving low velocity sensitivity without flash artifacts in thyroids, assist in cardiac or other applications.

Figure 1:
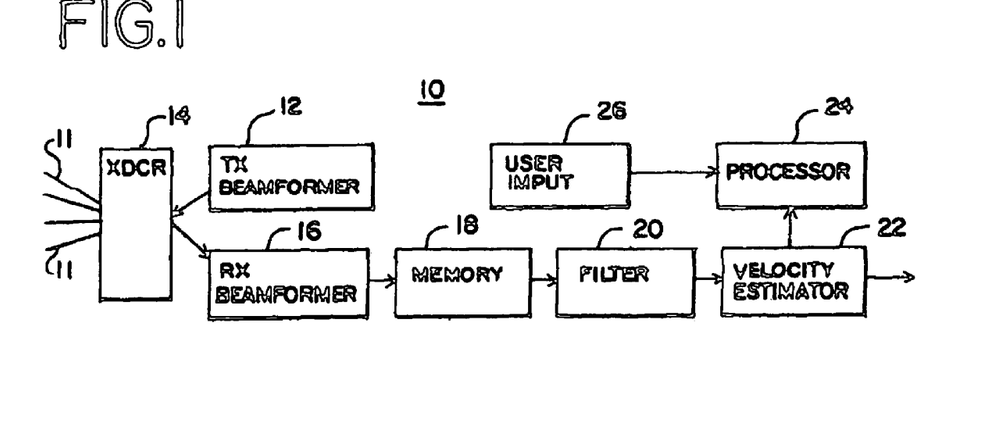
FIG. 1 is a block diagram of one embodiment of a system for determining velocity scale for ultrasound imaging.

FIG. 1 shows a system 10 for automatically determining velocity scale for ultrasound imaging. Setting the velocity scale appropriately may minimize aliasing. The system 10 includes a transmit beamformer 12, a transducer 14, a receive beamformer 16, a memory 18, a filter 20, a velocity estimator 22, a processor 24 and a user input 26. Additional, different or fewer components may be provided. For example, the system includes the velocity estimator 22 and processor 24 without the front-end components such as the transmit and receiver beamformers 12, 16. As another example, a scan converter and display are provided. In one embodiment, the system 10 is a medical diagnostic ultrasound system. In an alternative embodiment, the system 10 is a computer or workstation. In yet another embodiment, the velocity estimator 22 is part of a medical diagnostic ultrasound system or other medical imaging system, and the processor 24 is part of a separate work station or remote system.

The transmit beamformer 12 is shown separate from the receive beamformer 16. Alternatively, the transmit and receive beamformers 12, 16 may be provided with some or all components in common. Operating together or alone, the transmit and receive beamformers 12, 16 form beams of acoustic energy for scanning a one, two or three dimensional region. One or more scan lines 11 are scanned. Vector®, sector, linear or other scan formats may be used. A single receive beam is generated for each transmit beam. Alternatively, two or more receive beams are generated for each transmit beam. Data representing scan lines may be synthesized from coherent receive beam data, such as disclosed in U.S. Pat. No. 5,623,928, the disclosure of which is incorporated herein by reference. Fully populated control data sets for any of the transmit or receive beamformer parameters discussed herein are provided. Alternatively, sparse sets are used for real-time calculation of the control data, such as disclosed in U.S. Pat. No. 5,581,517, the disclosure of which is incorporated herein by reference.

The transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 is the transmit beamformer disclosed in U.S. Pat. No. 5,675,554, the disclosure of which is incorporated herein by reference. The transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A scan line focus is generated based on these beamforming parameters.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The receive beamformer 16 is a preamplifier, filter, phase rotator, delay, summer, base band filter, processor, buffers, memory, combinations thereof or other now known or later developed receive beamformer components. In one embodiment, the receive beamformer is one disclosed in U.S. Pat. Nos. 5,555,534, 5,921,932 and 5,685,308, the disclosures of which are incorporated herein by reference. Other analog or digital receive beamformers may be used.

The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

A control processor controls the various beamforming parameters for receive beamformation. The values provided for the beamformer parameters for the receive beamformer 16 are the same or different than the transmit beamformer 12. For example, an aberration or clutter correction applied for receive beam formation is different than an aberration correction provided for transmit beam formation due to differences in signal amplitude.

The receive beamformer 16 is operable to form receive beams in response to the transmit beams. For example, the receive beamformer 16 receives one or two receive beams in response to each transmit beam. The receive beams are collinear, parallel and offset or nonparallel with the corresponding transmit beams. A substantially same scan line accounts for patient movement or the use of overlapping beams.

The receive beamformer 16 outputs image data, data representing different spatial locations of a scanned region. The image data is coherent (i.e., maintained phase information) or incoherent. The data may be formed by processing received data, such as synthesizing scan lines (i.e., coherent combination), or other processes for generating data used to form an image from received information. For example, inter-beam phase correction is applied to one or more beams, and then the phase corrected beams are combined through a coherent (i.e., phase sensitive) filter to form synthesized ultrasound lines and/or interpolated between beams to form new ultrasound lines. Once the channel data is beamformed or otherwise combined to represent spatial locations along the scan lines 11, the data is converted from the channel domain to the image data domain.

For imaging motion, such as tissue motion or fluid flow, multiple transmissions and corresponding receptions are performed for a substantially same spatial location. Phase changes between the different receive events indicate the velocity of the tissue or fluid. A flow sample group corresponds to multiple transmissions for each of a plurality of scan lines 11. The scan lines 11 may be sparsely sampled, such as scanning every eighth, tenth or sixteenth scan line 11 multiple times for each flow sample grouping. The number of times a substantially same spatial location, such as a scan line 11, is scanned within a flow sample group is the flow sample count. The transmissions for different scan lines 11, different flow sample groupings or different types of imaging may be interleaved. The amount of time between transmissions to a substantially same scan line 11 within the flow sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a flow, color or velocity path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to base band and a programmable low pass filter response for removing or minimizing information at frequencies away from the base band. In other embodiments, the filter 20 is a low pass, high pass or band pass filter. The filter 20 identifies velocity information from slower moving tissue as opposed to fluids or alternatively reduce the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the velocity estimator 22.

The velocity estimator 22 is a Doppler processor or cross-correlation processor for estimating velocity. In one embodiment, the velocity estimator 22 allows time division multiplexing for determining multiple estimates of velocity substantially simultaneously. Parallel processing or sequential processing to obtain two or more velocity estimates representing a same spatial location may be used. In alternative embodiments, another device now known or later developed for estimating velocities from any or various input data may be provided. The velocity estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The velocity estimator 12 outputs velocity data that may include aliased information or velocities. Where an actual velocity is outside of the velocity scale (i.e. PRI) or range as a function of the Nyquist sampling frequency, the velocity data is aliased. Velocity information for a particular spatial location or a plurality of spatial locations (e.g. scan lines 11) is output. More than one signal sample may be provided for any given spatial location. For example, 1 to 12 samples are output for each spatial location. The velocity estimator 22 may also estimate energy and/or variance for each velocity estimate.

The velocity estimator 22 estimates multiple velocities from the received signals. For a spatial location, at least two velocities are estimated. One or more velocities are estimated from received signals for each pulse repetition interval. Different velocities for a same spatial location correspond to at least two different pulse repetition frequencies. The estimated velocities may or may not be aliased based on the actual velocity as compared to the pulse repetition frequency. Since velocities responsive to two or more pulse repetition intervals are estimated for the spatial locations, none, one, two, a subset, or all velocities may be aliased or not aliased. By providing a range of pulse repetition frequencies, the maximum or large velocity without aliasing may be identified for setting the velocity scale for subsequent imaging.

The pulse repetition frequency may correspond to actual differences in transmission timing or differences in received signals selected for estimating the velocity. For example, the velocity estimator 22 selects the different subsets of signals for different pulse repetition intervals from signals acquired with a same transmission pulse repetition interval the memory 18. As another example, the velocity estimator 22 identifies phase differences between signals associated with pairs of different transmission based pulse repetition intervals. By varying the pulse repetition frequency during transmission, a sign change in the velocity estimate or phase change may indicate aliasing. A pulse repetition interval greater than associated with aliased velocities may avoid aliasing. As yet another example, different velocities are estimated from different sets of received signals where each set is associated with a different transmitted pulse repetition frequency. Aliasing information associated with other non-transmitted pulse repetition frequencies may be derived from the received signals where multiple frequency pulses are transmitted. The filter 20 or another filter isolates information at two or more different frequencies for each set of signals. The velocity estimator 22 estimates velocities for each of the isolated sets of information.

The user input 26 is a keyboard, buttons, joystick, trackball, mouse, sliders, touch pad, combinations thereof or other now known or later developed input device. The user input 26 provides signals to the processor 24 or other components of the system 10 in response to user activation. For example, the signals from the user input 26 control configuration of the system 10 for flow or tissue velocity imaging. As another example, a button or other device is provided for single or one time activation of automated setting of the velocity scale. As yet another example, the user input 26 is used to select flow or tissue velocity imaging with periodic or multiple automatic dynamic settings of the velocity scale.

The processor 24 is a digital signal processor, a general processor, an application specific integrated circuit, field programmable gate array, control processor, digital circuitry, analog circuitry, combinations thereof or other now known or later developed device for implementing calculations, algorithms, programming or other functions. The processor 24 operates pursuant to instruction provided in the memory 18 or a different memory.

The processor 24 receives velocity estimates from the velocity estimator 22, such as initiating the transfer of estimates to the processor 24 in response to user input or automated triggers. The processor 24 determines a velocity scale as a function of the velocities associated with different pulse repetition intervals. In one embodiment, the processor 24 implements one or more of the algorithms, acts, steps, functions, methods or processes discussed below with respect to FIGS. 2-8, either by processing the data and/or controlling operation of other components of the system 10. For example, the processor 24 implements acts 36, 38 and/or 40 of FIG. 2. Different algorithms may be implemented, such as performing or controlling additional color post processing or selecting between types of flow or tissue motion imaging. Additional or multiple processors may be used to implement various aspects of the algorithms.

Figure 2:
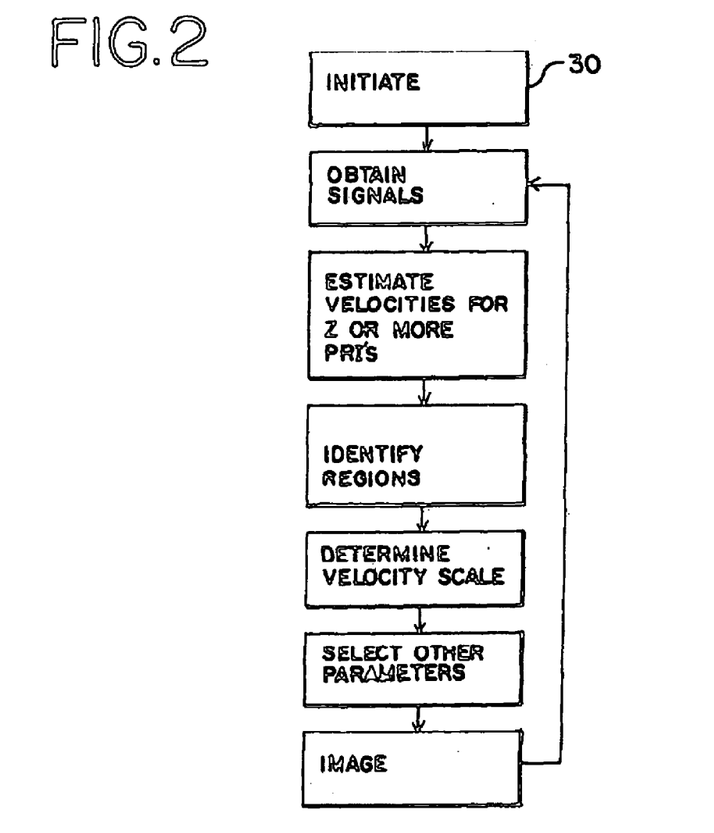
FIG. 2 is a flow chart diagram of one embodiment of a method for determining velocity scale for ultrasound imaging.

FIG. 2 shows a method for determining velocity scale for ultrasound imaging. The method is performed by the system 10 of FIG. 1 or a different system. The acts of FIG. 2 are performed in the order shown or a different order. Additional, different or fewer acts than shown in FIG. 2 may be used. For example, acts 30, 36, 40 and/or 42 are not provided. The acts of FIG. 2 described below may be implemented in different ways. Three example embodiments of the different implementations are shown, but other embodiments are possible.

In act 30, the process is initiated. For example, the obtaining of act 32, estimating of act 34 and determining of act 38 are started in response to user activation of automatic velocity scale setting. The user depresses a button once or whenever the velocity scale appears to result in undesired images. The process then automatically determines the velocity scale. Alternatively, the process begins in response to a trigger, such as based on data analysis or other signal.

In act 32, signals responsive to multiple transmissions along a substantially same scan line are obtained. The signals are obtained by transmission and reception, from a memory or from transfer over a bus or network. The received signals correspond to a same pulse repetition interval or two or more pulse repetition intervals.

In one embodiment, the signals are for portions of scan lines in a full sampling of a color or velocity region of interest. In another embodiment, the obtained signals correspond to sparse sampling of the velocity region of interest. For example, a sparsely sampled pilot flow sample group (e.g., every other, fourth, eighth, sixteenth or other number scan lines 11 with full or sparse range sampling) is obtained. The flow sample count (FSC) for each scan line is the same or different and is long or short, such as a long FSC of 64 or 128 samples. Greater or lesser sampling may be used, such as three or more samples. Multiple samples allow velocity estimation at several velocity scales substantially simultaneously. The sparse sampling facilitates identification of the velocity estimates for the entire velocity region of interest. Any frame-rate reduction due to the use of a large, or long, FSC may be insignificant as seen by the user due to the sparse sampling. The pilot flow sample group for velocity scale setting may or may not be executed on a continuous basis during scanning and may or may not include signals also used for velocity imaging.

In act 34, velocities are estimated from the signals as a function of different pulse repetition intervals. Signals responsive to different pulse repetition intervals are selected from a set of signals or acquired in response to different intervals. For example, the clutter filter is used to select different subsets of the signals for the different pulse repetition intervals. The selected signals may be clutter filtered, such as to isolate information associated with low, high or other velocities.

The phase change or average phase change between two or more signals is calculated for each pulse repetition interval. Two or more velocities are estimated for each spatial location and/or scan line 11 within the full or sparse sampling. One or more velocities are estimated for each pulse repetition interval. Two or more pulse repetition intervals are used, such as four, twelve or other number. The selected pulse repetition intervals are uniformly or non-uniformly spread throughout a likely range of velocity scales for a given type of imaging. For example, integer multiples of the PRI from 20 microsecond to 4800 microsecond, such as 80, 120, 160, 240, 320, 480, 640, 960, 1540, and 1920 microseconds for a frequency of 5 MHz, are provided for carotid imaging. As another example, integer multiples of the PRI from 20 microsecond to 4800 microsecond, such as 160, 240, 320, 480, 640, 960, 1540, 1920, and 2540 microseconds for a frequency of 5 MHz, are provided for thyroid or carotid imaging. As yet another example, integer multiples of the PRI from 20 microsecond to 4800 microsecond, such as 400, 800, 1600, 2400, 3200, 4000, and 4800 microseconds for a frequency of 2.5 MHz, are provided for liver imaging.

The estimated velocities are used without further processing. Alternatively, thresholds are applied to the velocities. For example, a low velocity threshold is applied. Velocities below the threshold are removed or set to another value, such as zero. As another example, energy for each of the spatial locations and pulse repetition frequencies is estimated. Where the energy is below a threshold, the velocity value is removed or set to another value, such as zero.

In act 36, regions of flow, such as desired fluid flow or tissue motion, are identified as a function of parameters responsive to the different pulse repetition intervals. The parameters include velocities, energies, variances or combinations thereof. Using the velocities, energies, variances combinations thereof or functions of one or more parameters, regions associated with flow are identified. Other spatial locations are determined as non-flow regions and not used in further processing or have the velocity values reset to a different value, such as zero.

Figure 3:
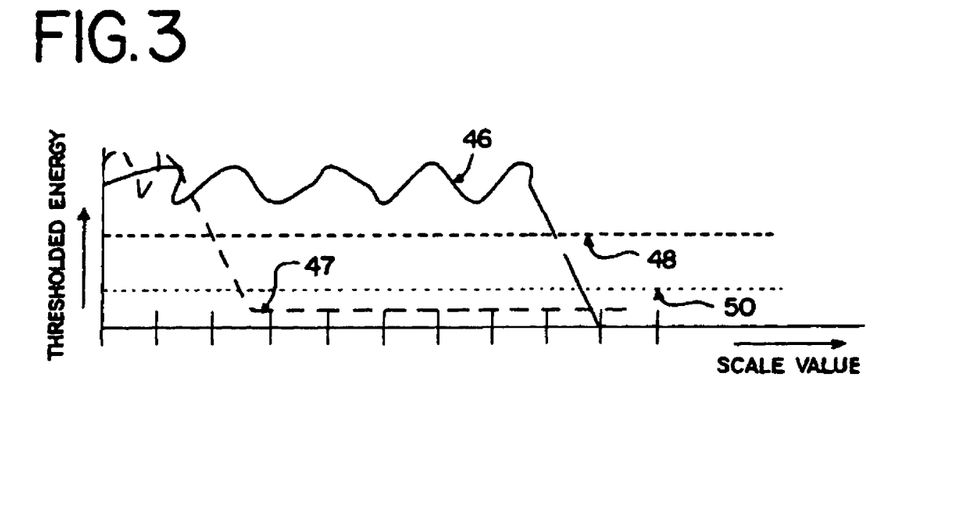
FIG. 3 is a graphical representation of exemplary energy response for identifying regions associated with flow.

In one embodiment, a mean and/or a median are used. For example, regions where a mean for each spatial location of the parameters responsive to the first and second pulse repetition intervals exceeds a first threshold and a median of the parameters is greater than a second threshold are selected as corresponding to actual flow. For each pulse repetition interval, a set of energy estimates are provided. The energy estimates are filtered, such as a spatial low pass filtering, and low values are removed by threshold comparison. The mean value or the median value of the energies at each spatial location is calculated. Alternatively other statistics on estimated parameters (e.g., velocity, variance, unfiltered energy) are used. Regions or spatial locations where the mean energy over the set of PRIs exceeds a threshold and where the median energy estimate is greater than zero are selected as associated with flow. FIG. 3 shows the median energy 46 and mean energy 48 for flow regions at a spatial location as a function of the pulse repetition interval. The median energy 47 and mean energy 50 for tissue regions is shown. Given the separation, the tissue and fluid flow information may be isolated. Flash suppression at low velocity scales is provided by this analysis of the pixel-wise parameter variation over the PRI's to identify the regions of valid color. For example, the median of the thresholded energy estimates over a group of PRI's remains close to zero for non-flow regions.

In act 38, a velocity scale is determined as a function of the velocities corresponding to different pulse repetition intervals and spatial locations. The velocity scale is set differently for different scan lines or regions for multiple scan lines. Alternatively, a single velocity scale for an entire velocity region of interest is automatically determined. Any now known or later developed function for determining the velocity scale may be used. For example, a maximum velocity for each spatial location is identified. The maximum velocities are averaged. The average maximum velocity is used as the pulse repetition interval or velocity scale for imaging. A scale is automatically determined for color Doppler imaging, such as continuous wave, pulsed wave, color Doppler velocity, color Doppler energy, convergent color Doppler, contrast agent imaging (e.g., bubble destruction, contrast velocity, agent destruction, power contrast), strain imaging, color Doppler tissue (e.g., tissue velocity, energy, and/or acceleration), or other flow or tissue motion imaging.

In act 40, one or more other parameters are automatically selected as a function of the velocity scale. For example, a filter parameter, a gating parameter, a gain parameter, a frequency parameter, a dynamic range parameter, line-density or number of beams or combinations thereof is selected as a function of the velocity scale. Automatic identification of some or all color settings is provided. In one embodiment, a function relating velocity scale to the other parameters is used. In another embodiment, the closeness of the velocity scale value to a preset velocity scale value identifies a range or related preset group. For example, the velocity scale is determined to be 0.1. A preset velocity scale with other corresponding parameter settings is provided for 0.11 and 0.08. Since 0.11 is the closest, the other parameters settings provided in the velocity scale 0.11 preset group are selected and used.

In act 42, velocity imaging is performed as a function of the velocity scale and any other automatically selected parameters. For example, color Doppler velocity imaging is performed with a pulse repetition interval set in act 38. The velocity imaging is for a sparse or full sampling of the velocity region of interest. Color values are displayed for the regions identified in act 36 and not for other spatial locations. Alternatively, different identification of regions is provided for imaging. The signals used for determining the velocity scale are not used for imaging, but may be included in signal sets for estimating imaging velocities.

In another embodiment, the maximum velocity information used to determine the scale setting is displayed. The maximum velocity for each spatial location in flow regions is selected from the velocities responsive to different pulse repetition intervals. The resulting image is displayed as subsequent pilot flow sample groups are acquired in act 32. Unaliased imaging is provided. Full sampling is provided. The signals are obtained with no or some interleaving with signals for other velocity imaging.

Since multiple pulse repetition intervals are provided to determine the maximum velocity for each spatial location, the imaging may have a reduced frame-rate as compared to color Doppler velocity imaging with the automatically determined velocity scale. The frame-rate reduction is due to the multiplicity of the different pulse repetition intervals. The reduction in frame rate may be minimized by allowing portions of the region of interest belonging to the same flow group to update at the highest frame-rate and then using temporal persistence to reduce lateral sampling variability. The highest frame-rate (e.g., 8 frames per second) corresponding to the flow sample count value used for flow estimation at each PRI is provided. For example, for a 64-pulse flow sample group and a flow sample count of 8, the frame-rate for the largest PRI ($PRI_{max}$) is 8 times smaller than the frame-rate for the smallest PRI ($PRI_{min}$). Yet the displayed frame-rate is the frame-rate corresponding to the largest PRI since 1 color frame is obtained per flow sample count. Interpolating each flow image by $PRI_{min}/PRI$ produces the highest frame rate for the entire image. As long as $PRI_{max}$ is greater than the Nyquist rate needed for the slowest flow scale, this frame-interpolation method may not result in significant information loss and may be similar to the highest-flow rate.

In one embodiment, color velocity imaging using the determined velocity scale continues without further determination or until the user triggers another automatic determination. FIG. 2 shows the process feeding back to act 32. In this embodiment, the velocity scale is dynamically determined in an on-going basis. The obtaining act 32, estimating act 34 and determining act 38 are performed periodically or in response to ultrasound information. For example, the velocity values provided in color Doppler imaging change in characteristic, such as average velocity increasing or decreasing by a particular amount. In response, the automated determination of the velocity scale is repeated automatically or without further user input. The pilot flow sample group is continuously or periodically updated.

For repetition of act 32, the sparse sampling may be guided by previously acquired information to reduce the number of needed transmissions or to optimize automated determination of the velocity scale. Statistics based on the previous frames are used to identify the location of the pilot flow sample group firings, density of firings and/or the number of firings (e.g., flow sample count). For example, the flow sample group is adjusted to scan lines in regions of strongest and/or highest velocity flow.

Figure 4:
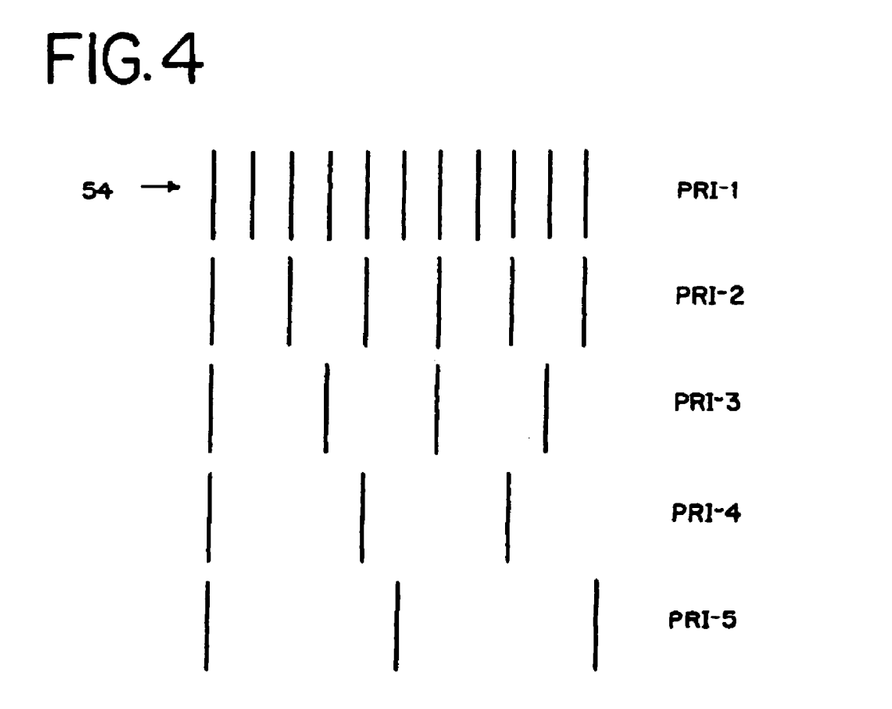
FIG. 4 is a graphical representation of a sequence of pulses used for estimating with different pulse repetition intervals in one embodiment.

FIG. 4 shows one embodiment of a method for automatic velocity scale calculation. Signals are obtained in response to a common pulse repetition interval 54. For example, a single long pilot flow sample group of 64 or 128 or other number of pulses with a small, such as the minimum, pulse repetition interval. Alternatively, 4, 5 or other number of flow sample groups are obtained with different pulse repetition intervals for each group. The flow sample groups are for a full or sparse sampling with a long flow sample count for automatic scale identification in color flow imaging.

Different velocities are estimated as a function of different pulse repetition intervals. As shown in FIG. 4, different signals (represented by different lines) are selected to form different pulse repetition intervals. The pulse repetition intervals are indicated by the distance between lines. FIG. 4 shows five different pulse repetition interval signal subsets from the original signal set 54. The different subsets of IQ samples at different pulse repetition intervals are chosen from the pilot flow sample group. For each subset, the parameters-of-interest (i.e. velocity and energy) are estimated after any clutter filtering and/or, thresholding of the subset.

Figure 5:
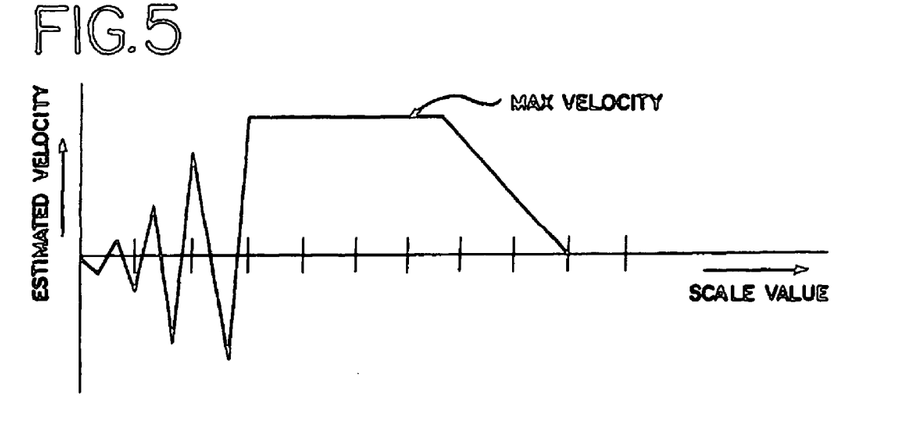
FIG. 5 is an exemplary graphical representation of velocity estimates for a spatial location as a function of pulse repetition intervals.
Figure 6:
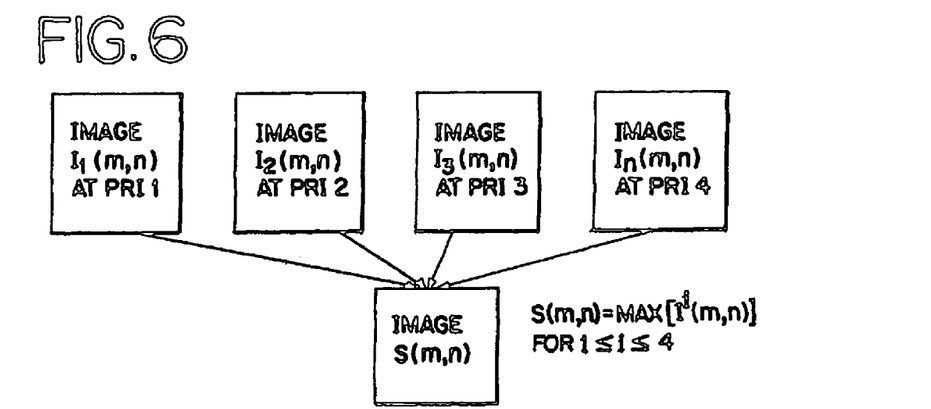
FIG. 6 is a graphical representation of one embodiment of velocity data selected as a function of different pulse repetition intervals.

To determine the velocity scale, the velocities are provided for each subset or pulse repetition interval and are represented in meters/sec or other units of measure. A maximum absolute value of the velocities for different pulse repetition intervals is selected for each spatial location. FIG. 5 shows the velocity as a function of pulse repetition interval for a single spatial location. The lower scale values or pulse repetition intervals show the velocity varying about the zero velocity, indicating possible aliasing. The maximum velocity is clipped by the clutter filter, but may not be clipped. FIG. 6 shows forming a maximum absolute velocity image from four velocity images associated with a respective four different pulse repetition intervals. The resulting collection of maximum absolute velocities provides a fully sampled or sparsely sampled velocity image or frame of data. The maximum velocities represent unaliased velocities. The resulting frame of maximum velocities provides unaliased velocity at every pixel in the velocity region of interest and/or region identified in act 36 of FIG. 2.

A mean, a median, both the mean and the median or other statistic of the selected maximum absolute values is calculated. For example, the mean of the maximum absolute velocities in the regions identified in act 36 of FIG. 2 is calculated. The velocity scale is determined as equal to the mean, median, combination of the mean and the median or other statistic. A function may be used to calculate the velocity scale from the statistic. In another embodiment, the pulse repetition intervals used to obtain the data in act 32 of FIG. 2 closest to the mean, median or both mean and median is selected as the velocity scale. The velocity scale is selected as the one of pulse repetition intervals that is closest to the mean absolute velocity.

Figure 7:
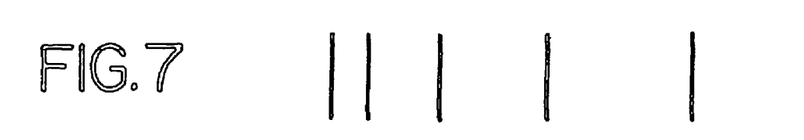
FIG. 7 is another graphical representation of a sequence of pulses used for estimating with different pulse repetition intervals in another embodiment.

FIG. 7 shows another embodiment of a method for automatic velocity scale calculation. Signals are obtained in response to a changing pulse repetition interval throughout multiple transmissions. FIG. 7 shows increasing pulse repetition intervals, but decreasing, arbitrary or variable changes may be used. For example, a long pilot flow sample group of 64 or 128 or other number of pulses is transmitted with linearly increasing pulse repetition interval. Non-linear change in the pulse repetition interval may be used, such as retaining the pulse repetition interval constant for the first few pulses and then increasing or decreasing the pulse repetition interval non-linearly or linearly. Flow sample interleaving is performed for different pulses in the flow sample group to minimize the frame rate reduction. Any time between two pulses in the same direction, greater than the minimum desired PRI, may be used to transmit additional pulses in a different direction.

Velocities are estimated from pulses separated by the same PRI. For example, FIG. 7 shows five signals with four pulse repetition intervals. The signals are clutter filtered, resulting in output groups sufficient to provide enough post-filtered samples for velocity estimation. The phase difference between each sequential pair of signals is determined. Where four different pulse repetition intervals are provided, four different phase differences result.

The progression of velocities from short PRI to long PRI is examined. The pulse repetition interval associated with a sign change in the progression of the velocities is identified. Pulse repetition intervals are similarly identified for the other spatial locations. The pulse repetition interval associated with the sign change indicates aliasing. The velocity corresponding to the smallest pulse repetition interval prior to the interval that corresponds to the sign change is selected.

The identified pulse repetition intervals or velocities are averaged or other statistics calculated. For example, a mean, a median or both the mean and the median of the identified pulse repetition intervals is calculated for the regions or spatial locations of interest. The velocity scale is determined as the mean, median or other statistic or is selected as the pulse repetition interval closest to the mean, median or both mean and median.

Figure 8:
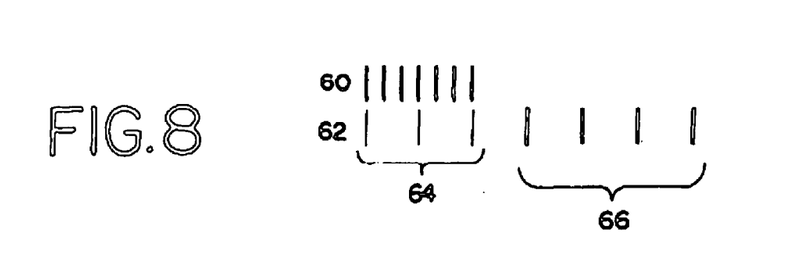
FIG. 8 is yet another graphical representation of a sequence of pulses used for estimating with different pulse repetition intervals in yet another embodiment.

FIG. 8 shows yet another embodiment of a method for automatic velocity scale calculation. Signals responsive to transmissions of broadband pulses along a substantially same scan line are obtained. On reception, the pulses are demodulated into two or more frequency bands. The broadband transmission can be achieved using coded pulses (e.g., chirp, Golay or Barker codes) or multi-modal pulses whose frequency bands are separate from each other, such as being at least 6, 10, 20, 40 or other number of decibels down from a peak. Waveform generation, filtering and/or transduction characteristics provide multi-modal acoustic energy.

The broadband pulses are transmitted multiple times in at least two sets. Each set is associated with a different pulse repetition frequency. FIG. 8 shows two sets 60, 62 of signals obtained with two different respective pulse repetition intervals (pri1, pri2). Some of the pulses may be used in both sets, such as the pulses 64 being used in both and the pulses 66 being used in only one or a fewer number of sets. The flow sample count may be short, such as between 8 and 16 samples.

To estimate the velocities associated with the different pulse repetition intervals, the signals of each set 60, 62 are filtered. Each set of received signals is filtered into two sets (f1, f2) for demodulation into two frequency bands. The received signal information associated with each of the frequency bands is substantially isolated from other frequency bands. For example, the received signals in each set are demodulated to one of the frequency bands. A narrow low pass filter is applied to the base band signals. The process is repeated for the other frequency band. Bandpass filtering may be used in other embodiments. Using two demodulations and two pulse repetition intervals, four sets of signals are provided.

Velocities are estimated for each of sets of signals. Energies may also be estimated. Four sets of velocities and energies are provided, two sets for each frequency band in the example above.

The velocity scale is determined as a function of the velocities. Additional pulse repetition intervals are calculated as a function of the transmitted pulse repetition intervals and a ratio of frequencies of the multi-modal pulses. One pseudo-PRI ($pri1_s$) is computed as $pri1_s = pri1 * f2/f1$. The velocities and energies (v2 and e2) associated with f2 are assigned to the pseudo-PRI. This results in velocity and energy estimates at the two PRI settings (pri1 and $pri1_s$) as (v1, e1) and (v2, e2). The process is repeated for a second pseudo-PRI associated with the second transmitted pulse repetition interval, pri2 thereby obtaining velocity and energy estimates at PRI settings (pri2 and $pri2_s$) as (v3, e3) and (v4, e4). This results in four velocity and energy estimates at four PRIs.

For each spatial location, the maximum absolute value of the velocities is selected. A mean, a median, both the mean and the median or other statistic of the selected maximum absolute values is computed. The velocity scale is determined as the pulse repetition interval (e.g., pri1, $pri1_s$, pri2, and $pri2_s$) closest to the mean, median, both mean and median or other statistic. Other relational functions may be used.

The frequency that corresponds to the selected PRI from the set of PRI's (pri1, $pri1_s$, pri2, and $pri2_s$ etc.), is automatically used for subsequent frames during color flow imaging. Alternatively, from the set of multiple demodulation frequencies obtained for the selected PRI; the frequency that produces the color estimates with the highest SNR is used. The SNR is computed from the regions of valid color or motion within the ROI.

The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining velocity scale for ultrasound imaging, the method comprising:
   obtaining signals responsive to multiple transmissions along a substantially same scan line;
   estimating first and second velocities from the signals as a function of first and second different pulse repetition intervals, respectively;
   determining a velocity scale as a function of the first and second velocities; and
   imaging as a function of the velocity scale.

2. The method of claim 1 wherein estimating the first and second velocities comprises estimating the first and second velocities from the signals for a substantially same spatial location on the scan line.

3. The method of claim 1 further comprising:
   initiating the obtaining, estimating and determining in response to user activation of automatic scale setting.

4. The method of claim 1 further comprising:
   repeating the obtaining, estimating and determining periodically or in response to ultrasound information, the repetition of obtaining being a function of the first and second velocities.

5. The method of claim 1 further comprising:
   identifying regions of flow as a function of parameters responsive to the first and second pulse repetition intervals, the parameters comprising the first and second velocities, first and second energies, first and second variances or combinations thereof.

6. The method of claim 5 wherein identifying comprises selecting regions where a mean for each spatial location of the parameters responsive to the first and second pulse repetition intervals exceeds a first threshold and/or a median of the parameters is greater than a second threshold.

7. The method of claim 1 further comprising:
   selecting a filter parameter, a gating parameter, a gain parameter, a frequency parameter, a dynamic range parameter, a line-density, a number of beams or combinations thereof as a function of the velocity scale; and
   wherein imaging comprises velocity imaging as a function of the velocity scale and the selected parameter.

8. The method of claim 1 wherein obtaining comprises sparsely sampling a velocity region of interest;
   further comprising:
   wherein imaging comprises velocity imaging as a function of the velocity scale with relatively full sampling of the velocity region of interest.

9. The method of claim 1 wherein:
   obtaining comprises obtaining the signals in response to a common pulse repetition interval, the common pulse repetition interval being a same or different interval than the first or second pulse repetition intervals;
   estimating the first and second velocities comprises selecting signals associated with the first and second pulse repetition intervals, respectively; and
   determining the velocity scale comprises:
      selecting a maximum absolute value of the first velocity or the second velocity;
      repeating the selecting for each of a plurality of spatial locations;
      calculating a mean, a median or both the mean and the median of the selected maximum absolute values; and
      determining the velocity scale as a one of the first and second pulse repetition intervals closest to the mean, median or both mean and median.

10. The method of claim 1 wherein:
    obtaining comprises obtaining the signals in response to a changing pulse repetition interval throughout the multiple transmissions, the changing pulse repetition interval including the first and second pulse repetition intervals at different times;
    estimating the first and second velocities comprises identifying first and second phase differences between signals associated with the first and second pulse repetition intervals; and
    determining the velocity scale comprises:
       identifying one of the first and second pulse repetition intervals corresponding to a sign change in the first and second phase differences;
       repeating the identifying for each of a plurality of spatial locations;
       calculating a mean, a median or both the mean and the median of the identified ones of the first and second pulse repetition intervals; and
       determining the velocity scale as a one of the first and second pulse repetition intervals closest to the mean, median or both mean and median.

11. The method of claim 1 wherein:
    obtaining signals comprises obtaining signals responsive to the multiple transmissions including first and second sets of multiple transmissions, the first set corresponding to a third pulse repetition interval and the second set corresponding to a fourth pulse repetition interval, the signals responsive to at least two demodulation frequencies obtained from broadband pulses;
    estimating first and second velocities comprises:
       filtering signals responsive to the first set of multiple transmissions at the third pulse repetition interval into first and second sets of signals;
       filtering signals responsive to the second set of multiple transmissions at the fourth pulse repetition interval into third and fourth sets of signals; and
       estimating velocities for each of the first, second, third and fourth sets of signals, the first velocity being in a first one of the sets of signals and the second velocity being in a different second one of the sets of signals; and
    determining the velocity scale comprises:
       calculating a fifth pulse repetition interval as a function of the third pulse repetition interval and a ratio the demodulation frequencies;
       calculating a sixth pulse repetition interval as a function of the fourth pulse repetition interval and the ratio of the demodulation frequencies, the first pulse repetition interval being one of the third, forth, fifth or sixth pulse repetition intervals and the second pulse repetition interval being a different one of the third, forth, fifth or sixth pulse repetition intervals;

selecting a maximum absolute value of the first velocity or the second velocity;

repeating the selecting for each of a plurality of spatial locations;

calculating a mean, a median or both the mean and the median of the selected maximum absolute values; and determining the velocity scale as a one of the first and second pulse repetition intervals closest to the mean, median or both mean and median.

12. The method of claim 1 wherein determining the velocity scale comprises determining difference between a maximum and minimum velocity estimation.

13. A system for determining velocity scale for ultrasound imaging, the system comprising:

a memory operable to store signals responsive to multiple transmissions along a substantially same scan line;

a velocity estimator operable to estimate first and second velocities from the signals as a function of first and second different pulse repetition intervals, respectively; and a processor operable to determine a velocity scale as a function of the first and second velocities.

14. The system of claim 13 further comprising a user input, the processor operable to initiate the determination of the velocity scale in response to the user input.

15. The system of claim 13 wherein the processor is operable to repeat determining of the velocity scale periodically or in response to ultrasound information.

16. The system of claim 13 wherein the processor is operable to identify regions of flow as a function of parameters responsive to the first and second pulse repetition intervals, the parameters comprising the first and second velocities, first and second energies, first and second variances or combinations thereof, the regions being where a mean for each spatial location of the parameters responsive to the first and second pulse repetition intervals exceeds a first threshold.

17. The system of claim 13 wherein the processor is operable to select a filter parameter, a gating parameter, a gain parameter, a frequency parameter, a dynamic range parameter or combinations thereof as a function of the velocity scale, and wherein the velocity estimator is operable for imaging as a function of the velocity scale and the selected parameter.

18. The system of claim 13 wherein the signals are responsive to a common pulse repetition interval, the common pulse repetition interval being a same or different interval than the first or second pulse repetition intervals;

wherein the velocity estimator is operable to select the signals associated with the first and second pulse repetition intervals, respectively; and wherein the processor is operable to select a maximum absolute value of the first velocity or the second velocity, repeat the selecting for each of a plurality of spatial locations, calculate a mean, a median or both the mean and the median of the selected maximum absolute values, and determine the velocity scale as a one of the first and second pulse repetition intervals closest to the mean, median, an existing set of presets or combinations thereof.

19. The system of claim 13 wherein the signals are responsive to a changing pulse repetition interval throughout the multiple transmissions, the changing pulse repetition interval including the first and second pulse repetition intervals at different times;

wherein the velocity estimator is operable to identify first and second phase differences between signals associated with the first and second pulse repetition intervals; and wherein the processor is operable to identify one of the first and second pulse repetition intervals corresponding to a sign change in the first and second phase differences, repeat the identifying for each of a plurality of spatial locations, calculate a mean, a median or both the mean and the median of the identified ones of the first and second pulse repetition intervals, and determine the velocity scale as a one of the first and second pulse repetition intervals closest to the mean, median or both mean and median.

20. The system of claim 13 wherein the signals are responsive to the multiple transmissions including first and second sets of multiple transmissions, the first set corresponding to a third pulse repetition interval and the second set corresponding to a fourth pulse repetition interval, the signals responsive to at least two demodulation frequencies obtained from a broadband transmit;

wherein the velocity estimator is operable to filter signals responsive to the first set of multiple transmissions at the third pulse repetition interval into first and second sets of signals, filter signals responsive to the second set of multiple transmissions at the fourth pulse repetition interval into third and fourth sets of signals, and estimate velocities for each of the first, second, third and fourth sets of signals, the first velocity being in a first one of the sets of signals and the second velocity being in a different second one of the sets of signals; and wherein the processor is operable to calculate a fifth pulse repetition interval as a function of the third pulse repetition interval and a ratio of demodulation frequencies, calculate a sixth pulse repetition interval as a function of the fourth pulse repetition interval and the ratio of demodulation frequencies, the first pulse repetition interval being one of the third, forth, fifth or sixth pulse repetition intervals and the second pulse repetition interval being a different one of the third, forth, fifth or sixth pulse repetition intervals, select a maximum absolute value of the first velocity or the second velocity, repeat the selecting for each of a plurality of spatial locations, calculate a mean, a median or both the mean and the median of the selected maximum absolute values, and determine the velocity scale as a one of the first and second pulse repetition intervals closest to the mean, median or both mean and median.

21. The system of claim 13 wherein the processor is operable to determine the velocity scale by setting a third pulse repetition interval the same as or different than either of the first or second pulse repetition intervals.

22. A method for determining velocity scale for ultrasound imaging, the method comprising:

obtaining signals responsive to at least two frequency bands using multiple demodulations of signals obtained from broadband pulses along a substantially same scan line;

determining a velocity scale as a function of the signals; and imaging as a function of the velocity scale.

23. The method of claim 22 wherein the signals are responsive to a sparsely sampled flow group transmitted along scan lines that correspond to valid regions of color identified in response to color frames.

24. The method of claim 22 wherein the at least two frequency bands correspond to first and second frequency bands; further comprising:

filtering the signals in first and second passes to obtain first and second sets corresponding to the first and second frequency bands, respectively; and estimating first and second velocities from the first and second sets, respectively.

25. The method of claim 22 wherein obtaining comprises obtaining signals responsive to first and second sets of multiple transmissions, the first set corresponding to a first pulse repetition interval and the second set corresponding to a second pulse repetition interval.

26. The method of claim 22 wherein obtaining signals comprises obtaining signals responsive to first and second sets of multiple transmissions, the first set corresponding to a first pulse repetition interval and the second set corresponding to a second pulse repetition interval;

further comprising:
filtering signals responsive to the first set of multiple transmissions at the first pulse repetition interval into first and second sets of signals;
filtering signals responsive to the second set of multiple transmissions at the second pulse repetition interval into third and fourth sets of signals; and
estimating velocities for each of the first, second, third and fourth sets of signals; and
wherein determining the velocity scale comprises:
calculating a third pulse repetition interval as a function of the first pulse repetition interval and a ratio of demodulation frequencies;
calculating a fourth pulse repetition interval as a function of the second pulse repetition interval and the ratio of demodulation frequencies;
selecting a maximum absolute value from the velocities for the first, second, third and fourth sets of signals for each of a plurality of spatial locations;
calculating a mean, a median or both the mean and the median of the selected maximum absolute values; and
determining the velocity scale as a one of the first, second, third or fourth pulse repetition intervals closest to the mean, median or both mean and median.

27. The method of claim 22 wherein obtaining the signals comprises obtaining the signals in response to multi-modal transmit pulses.

28. The method of claim 22 wherein obtaining the signals comprises obtaining the signals in response to coded transmit pulses.

29. The method of claim 22 further comprising:
automatically selecting an imaging frequency from among the multiple demodulations as a function of a signal-to-noise ratio SNR.

* * * * *